United States Patent [19]
Massoud

[11] Patent Number: 6,077,513
[45] Date of Patent: Jun. 20, 2000

[54] DRUG FOR TREATMENT OF BILHARZIASIS (SCHISTOSOMIASIS)

[76] Inventor: Ahmed Mohamed Ali Massoud, 12 Potross Ghali Street-Heliopolis, Cairo, Egypt

[21] Appl. No.: 08/848,908

[22] Filed: May 1, 1997

[51] Int. Cl.$^7$ .................................................. A61K 35/78
[52] U.S. Cl. ...................... 424/195.1; 424/405; 424/439; 424/456; 426/651
[58] Field of Search ................................ 424/195.1, 405, 424/439, 456; 426/651

[56] References Cited

U.S. PATENT DOCUMENTS

| | | | |
|---|---|---|---|
| 4,719,111 | 1/1988 | Wilson | 424/195.1 |
| 4,780,316 | 10/1988 | Brox | 424/456 |
| 5,248,503 | 9/1993 | Emanuel-King | 424/195.1 |
| 5,350,774 | 9/1994 | Palou | 424/195.1 |
| 5,665,386 | 9/1997 | Benet et al. | 424/451 |

FOREIGN PATENT DOCUMENTS 3066623  3/1991  Japan .

OTHER PUBLICATIONS

Massoud et al. Am. J. Trop. Med. Hyg., vol. 55 (2), Suppl., pp. 233–234, Dec. 1996.
Kakrani et al. Fitoterapia, vol. 55 (4), pp. 232–234, abstract enclosed, 1984.
Lee and Lamm, Contact Dermatitis, vol. 28 (2), pp. 89–90, 1993.
Michie and Cooper, J. Roy Soc. Med., vol. 84, pp. 602–604, 1991.
Zygmunt and Claeson, Phytother. Res vol. 5 (3), pp. 142–144, 1991.

*Primary Examiner*—Leon B. Lankford, Jr.
*Assistant Examiner*—Christopher R. Tate
*Attorney, Agent, or Firm*—Thomas R. Vigil

[57] ABSTRACT

The method of extracting volatile oils from *Commiphora molmol* includes the steps of grinding up the *Commiphora molmol* plant; covering the ground up plant with a layer of water to create a mixture of plant and water; passing steam through the mixture of water and plant; condensing volatile oil from the steam in a condensing chamber; and, separating the layer of oil from the aqueous layer therebeneath.

The oil fractions can also be obtained by extracting myrrh powder using petroleum ether; and, evaporating the petroleum ether to obtain the oil fraction.

The method of extracting resins from *commiphora molmol* after volatile oils have been separated therefrom including the steps of treating the myrrh powder with alcohol; evaporating the alcohol extract; precipitating the resin collected; washing the resin; and, drying the resin. Alternatively, the myrrh powder can be treated with myrrh powder with petroleum ether; extracting the ether with methanol; and, evaporating the methanol to obtain a resin fraction. The oleogum-resin obtained is useful as an anti-schistosomal agent.

6 Claims, 9 Drawing Sheets ated smooth muscle relaxing effect on the isolated guinea pig ileum (Claeson et al., 1991). The resin (myrrh) is widely used in Somalia to treat stomach complaints and diarrhoea (Zygmunt and Claeson, 30 1991). Sesquiterpene T-Cadinol caused bacterial lysis and subsequent fatal loss of intracellular components in *Staphylococcus aureus* (Claeson et al., 1992). Myrrh, natural gum resins, used to relieve pain and swelling due to traumatic injury by patching test (Lee and Lam, 1993). Myrrh has found recent pharmacological application in the reduction of cholesterol and triglycerides (Michie and Cooper, 1991). Tincture of myrrh is used for therapy of aphthous ulcer (stomatitis ulcer) (Pesko, 1990).

DRUG FOR TREATMENT OF BILHARZIASIS (SCHISTOSOMIASIS)

BACKGROUND OF THE INVENTION

1. Field of the Invention

The present invention relates to the anti-schistosomal activity of myrrh (oleogum-resin obtained from the stem of *Commiphora molmol*) and its derivatives. Volatile oils extracted from the plant were discovered to have excellent anti-schistosomal activity. Resins extracted from the plant also were discovered to have an excellent anti-schistosomal activity. Both volatile oils and resins collected together in a certain ratio were found to have a very potent effect as a schistosomicidal agent without any signs of hepatotoxicity.

2. Description of the Related Art

Schistosomiasis is increasing in incidence despite concerted efforts to control the disease in all the endemic areas. While a multiprolonged method of control using health education, sanitation and snail control has been used, chemotherapy and chemoprophylaxis play the most important and crucial role in containing/preventing the transmission of the disease.

Praziquantel is currently the drug of choice for the treatment of any kind of schistosomiasis. The only limitation is the cost which restricts its use in many developing countries.

While effective, safe drugs for mass chemotherapy are being developed, the problem of therapeutic failure and drug resistance is being reported from certain developing countries.

Under this circumstances, alternative drugs must be resorted to (Skekhar, 1991).

Mass treatment, a crucial goal in the eventual control of schistosomiasis, awaits a well-tolerated and nontoxic drug that will ultimately prove to be effective where cure is definite.

SUMMARY OF THE INVENTION

The present invention relates to the use of myrrh and its derivatives as an antischistosomal drug.

Myrrh is an oleogum-resin obtained from the stem of *Commiphora molmol* (Family Burseraceae) growing in north-east Africa and Arabia. The drug is chiefly collected in Somali land. The name "myrrh" is probably derived from the Arabic and Hebrew word mur, which means bitter. Much of the secretion is obtained by spontaneous exudation from the cracks and fissures which commonly form in the bark, and some is obtained from incisions made by the Somalis. The yellowish-white, viscus fluid soon hardens in the great heat to reddish-brown masses. Myrrh contains 7–17% of volatile oil, 25–40% of resin, 57–61% of gum and some 3–4% of impurities.

Plant mixture extract may prove to be a useful therapeutic agent in the treatment of NIDDM (Al-Awadi et al., 1991) *Commiphora molmol* (myrrh) was found to be equivalent to those of the standard cytotoxic drug cyclophosphamide (Qureshi et al., 1993). Treatment with *Commiphora molmol* (myrrh) (250 and 500 mg/kg/day) was found to be cytotoxic in Ehrlich solid tumors cells. The anti-tumor potential of *C.molmol* was comparable to the standard cytotoxic drug cyclophosphamide.

The present study confirmed the cytotoxic and anticarcinogenic potential of C.molmol (Al-Harbi et al., 1994). T-Cadinol; a sesquiterpene active constituent of scented myrrh was shown to have a concentration - dependent Myrrh is approved by the FDA for food use (21 CFR 172.510), and was given GRAS status as a flavor ingredient (No. 2765) by FEMA. The Council of Europe (1981) included myrrh in the list of plants and parts thereof, which are acceptable for use in foods (Food chem Technol., 1992). dr

DESCRIPTION OF THE PREFERRED EMBODIMENT(S)

Figure 1:
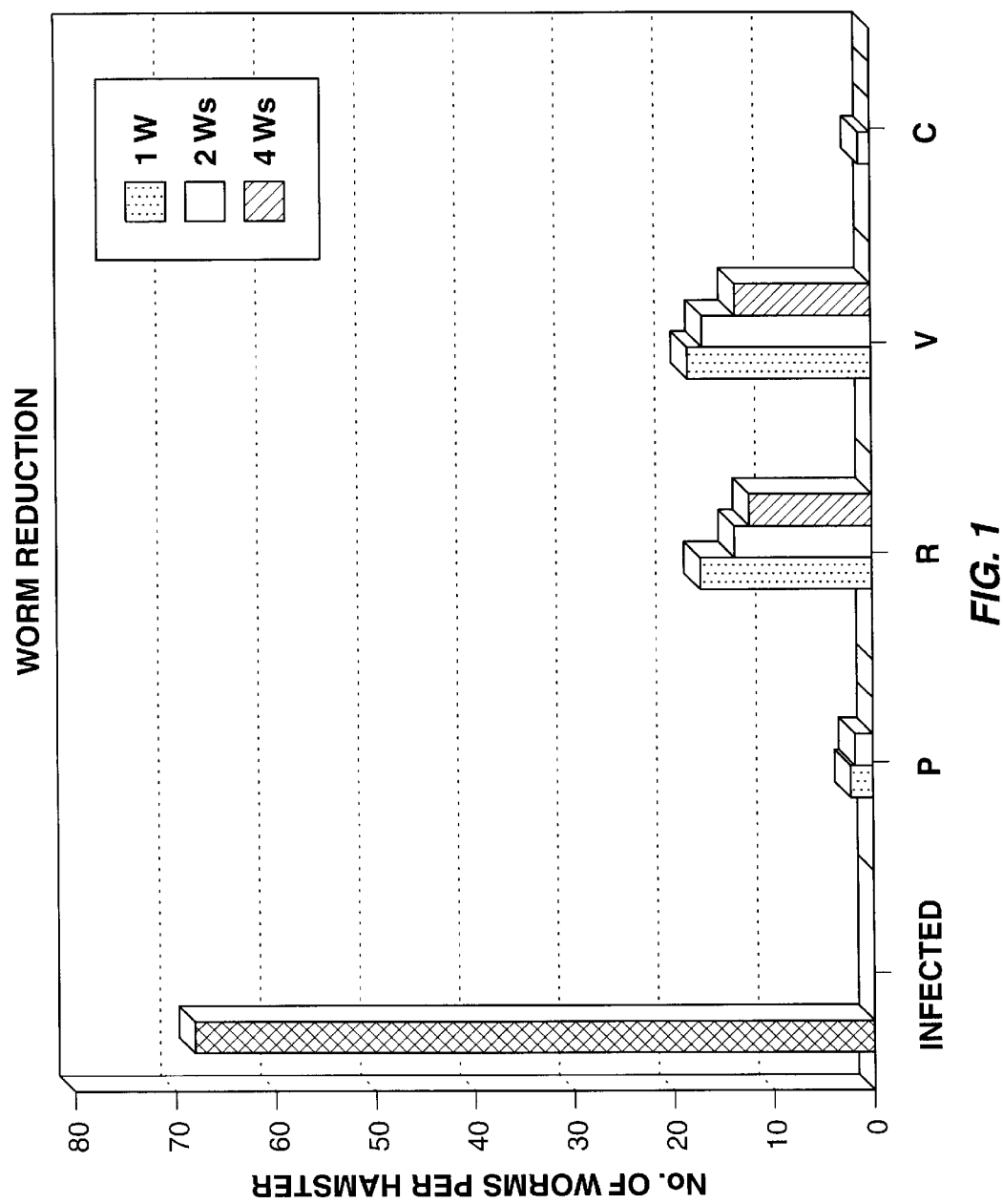
FIG. 1 is a graph of number of worms per hamsters versus treatment with crude plant, resin and volatile oil in combination thereof.

The present invention utilizes myrrh, namely the oleogum-resin obtained from the stem of *Commiphora molmol*. The main ingredients of the crude plant include:

1. Volatile oils, containing heerabolene, cadinene, elemol, eugenol, cuminaldehyde, numerous furanosesquiterpenes including furanodiene, furanodienone, curzerenone, lindestrene, 2-methoxyfuranodiene and other derivatives.

2. Resins, including [[alpha]]-, [[beta]]- and [[gamma]]-commiphoric acids, commiphorinic acid, heeraboresene, [[alpha]]- and [[beta]]-heerabomyrrhols and commiferin.

3. Gums, composed of arabinose, galactose, xylose and 4-0-methylglucuronic acid.

The ingredients or compounds from this plant which provide anti-schistosomal activity are prepared in the following manner:

1. Volatile Oils
   a. Water and steam distillation, the drug is ground and immediately covered with a layer of water and steam is passed through the mixture by pipes. The volatile oil is condensed in the condensing chamber. The oil layers are separated from the aqueous layer.

b. Petroleum ether extraction, 1 kg of Myrrh powder is extracted with 3 Ls petroleum ether 3 times; 1 L. each time. Evaporate the petroleum ether to get the oil fraction.

2. Resins a. Alcohol extraction, the powdered drug after separation of volatile oil component is exhausted with ethanol. Alcohol extract is evaporated and the precipitated resin is collected, washed and dried.

b. Petroleum ether extraction, the powdered drug after extraction with petroleum ether is extracted with methanol 3 times; 200 ml each time. Evaporate the methanol to get the resin fraction.

EXPERIMENTATION

Experiments were carried out with five groups of hamsters (30 each) experimentally infected with 120±10 cercariae of an Egyptian strain of *S. mansoni* (De Witt, 1965) The weight of animals used in this study ranged from 80 to 120 gm and their age ranged from 8 to 10 weeks.

One group was treated by the crude plant emulsion "myrrh", 180 mg/kg. A second group was treated with the resin active gradient separated from the plant 60 mg/kg. The third group was treated with the volatile oil active gradient separated from the plant 30 mg/kg. A fourth group was treated with a combination of resin and volatile oil (60 mg/kg and 30 mg/kg respectively). Treatment started in all groups eight weeks post infection. The fifth group served as infected non-treated control group. In all treated groups, the drug preparations were given in an emulsion form with distilled water on three equally divided daily oral doses.

Five other groups of non-infected normal hamsters (30 each) were tested; four groups were treated with the same drug regimens as in the infected groups and the first one served as normal non-infected non-treated control group.

Hamsters were sacrificed by decapitation after fasting overnight one week, two weeks and four weeks after the end of treatment (10 animals each time in each group). Blood was collected, centrifuged for separation of serum for estimation of enzymes; alkaline phosphatase, ALT (GPT) and AST (GOT).

The therapeutic efficacy of the drugs was tested parasitologically by studying:

1. Worm load: immediately after decapitation, the worms from infected animals were collected counted from the portal and mesenteric veins as well as from the liver by perfusion (Pellegrino and Squeira, 1956).

2. Oogram studies: including microscopic examination of press preparations from intestinal fragments of infected animals (Pellegrino and Faria, 1965) Three fragments of whole intestine wall (small intestine) each measuring 1 cm length were cut off. One hundred eggs were counted per each fragment and classified according to the four different stages of their development (Pellegrino et al., 1962).

Eggs of the first stage have small embryos occupying one third of the diameter of the eggs. Embryos of the second stage are slightly larger than half the transverse diameter. Eggs of the third stage show an embryo whose size corresponds to two-thirds the diameter of the eggs. Eggs of the fourth stage show embryos that occupy the whole of the egg shell. The mature eggs contain a fully developed miracidium with signs of miracidia vitality (activity of flame cells and beating of cilia).

Dead eggs appeared semitransparent, granular, darkened with retracted embryos. The mean percentage of each developmental stage of eggs in the three fragments was calculated in relation to 300 eggs.

A dose of any schistosomicidal drug is considered to be effective against *S.mansoni* worms when the oogram showed 50% or more mature eggs and absence of one or more stages of immature eggs. Pellegrino et al., 1962, stated that active schistosomicidal drugs are able to produce an increase in the percentage of mature eggs in relation to viable eggs up to 100% after variable periods.

3. Egg count in liver and intestine: Ova of homogenous emulsions were counted after being spread on slides and number of ova per gram tissues were calculated (Pellegrino and Faria, 1965).

RESULTS

Figure 2:
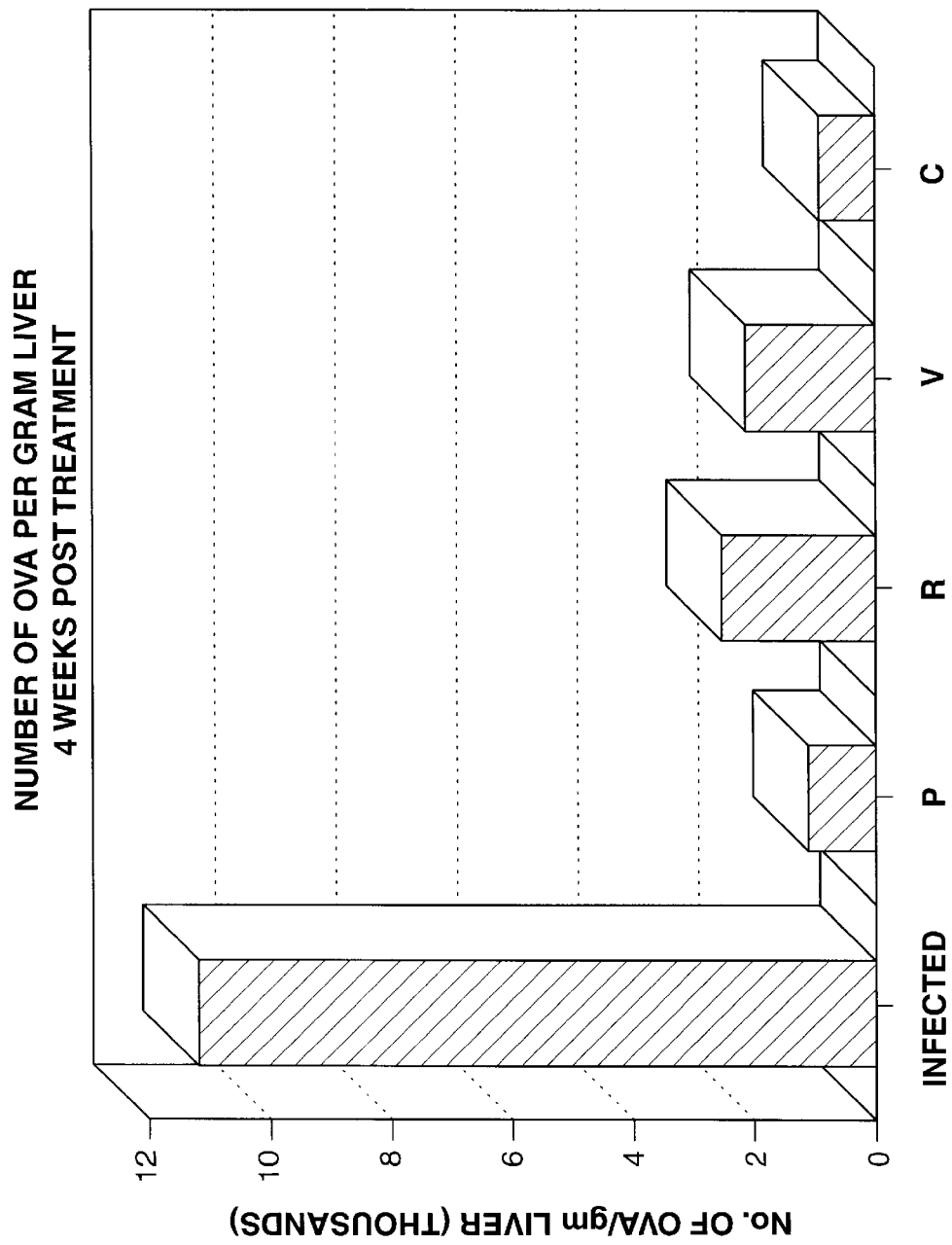
FIG. 2 is a graph of number of ova per gram of liver versus treatment with crude plant, resin and volatile oil in combination thereof.
Figure 3:
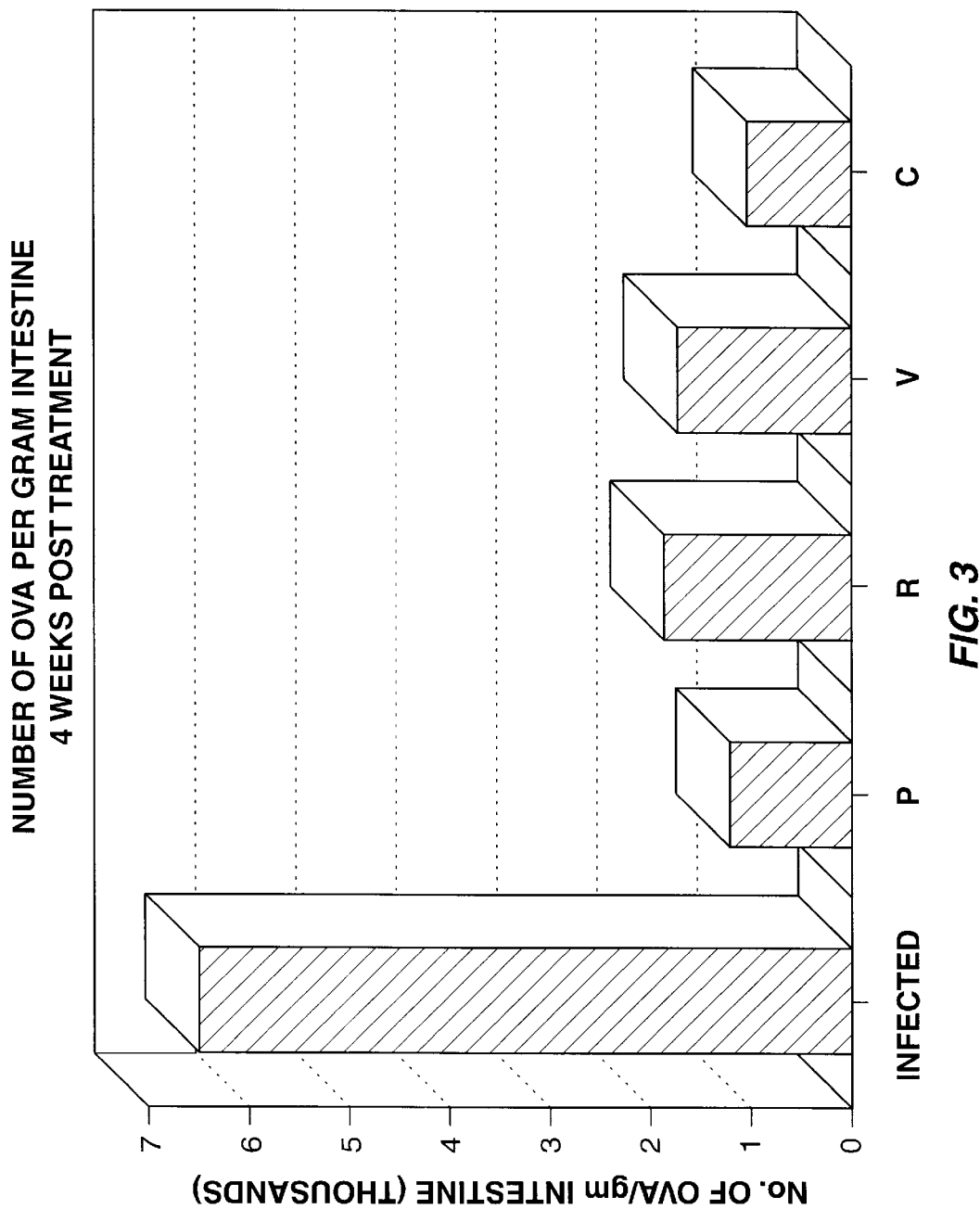
FIG. 3 is a graph of number of ova per gram of intestines versus treatment with crude plant, resin and volatile oil in combination thereof.
Figure 4:
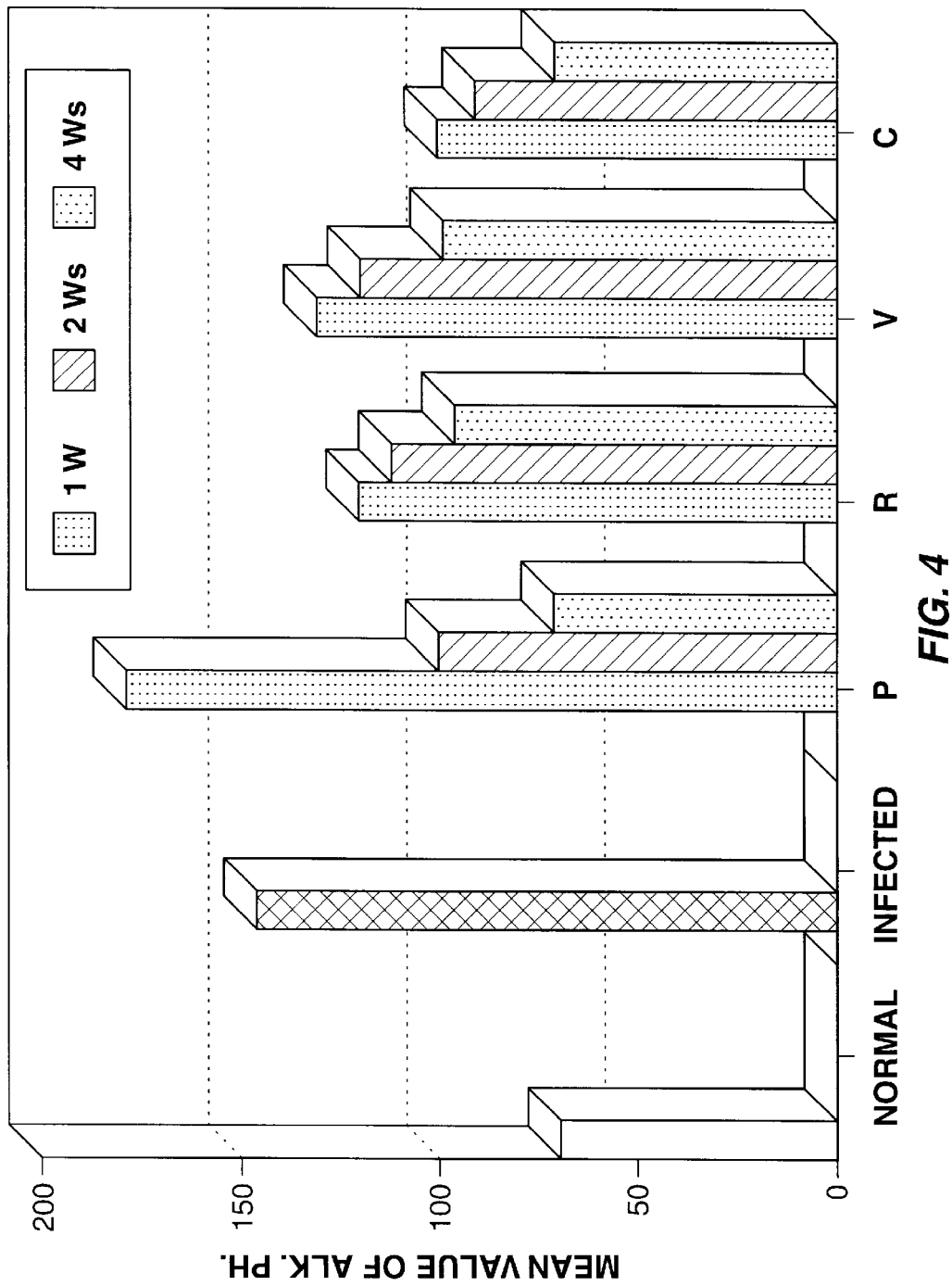
FIG. 4 is a graph of the effect of treatment on alkaline phosphatase in infected groups.
Figure 5:
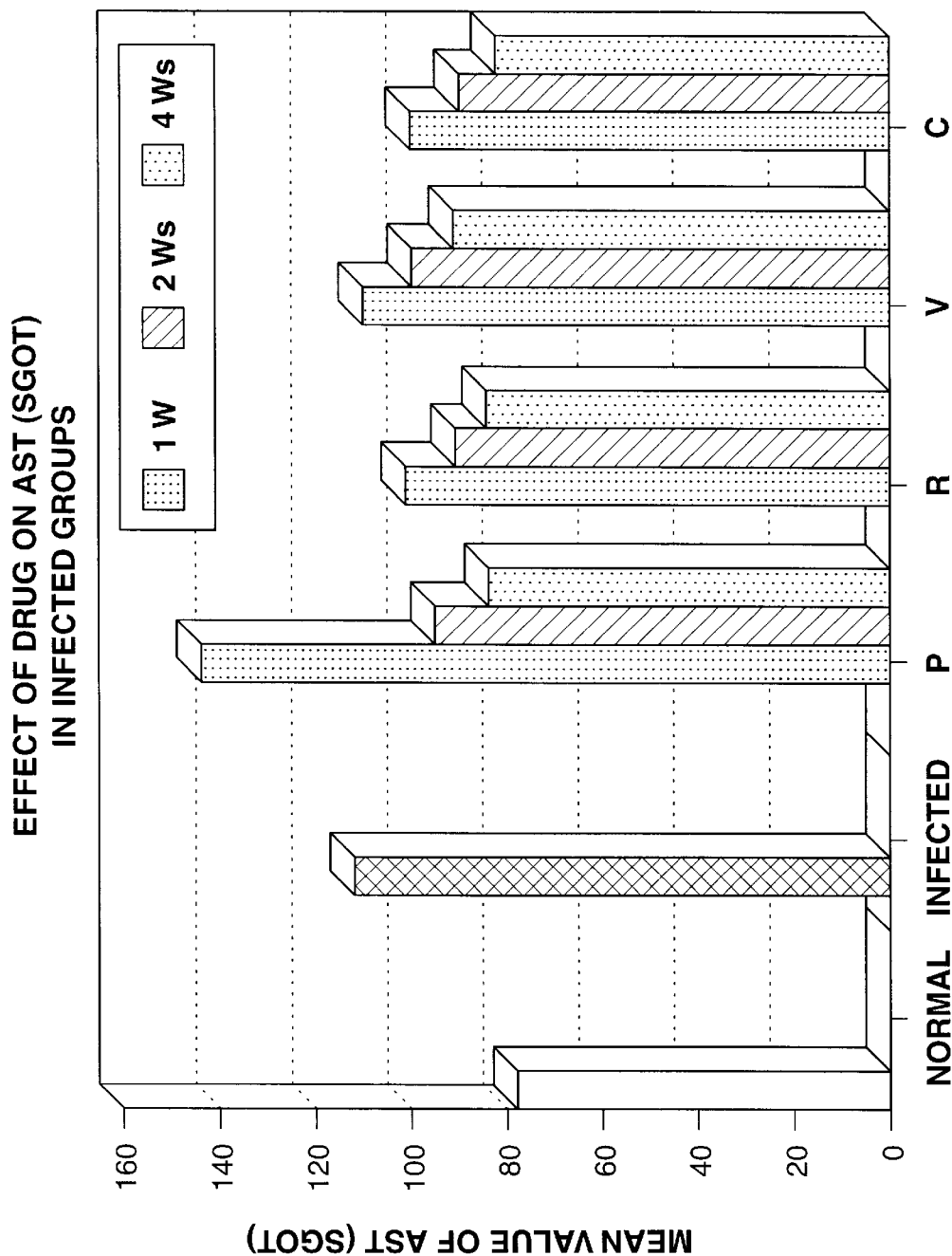
FIG. 5 is a graph of the effect of treatment on AST (SGOT) in infected groups.
Figure 6:
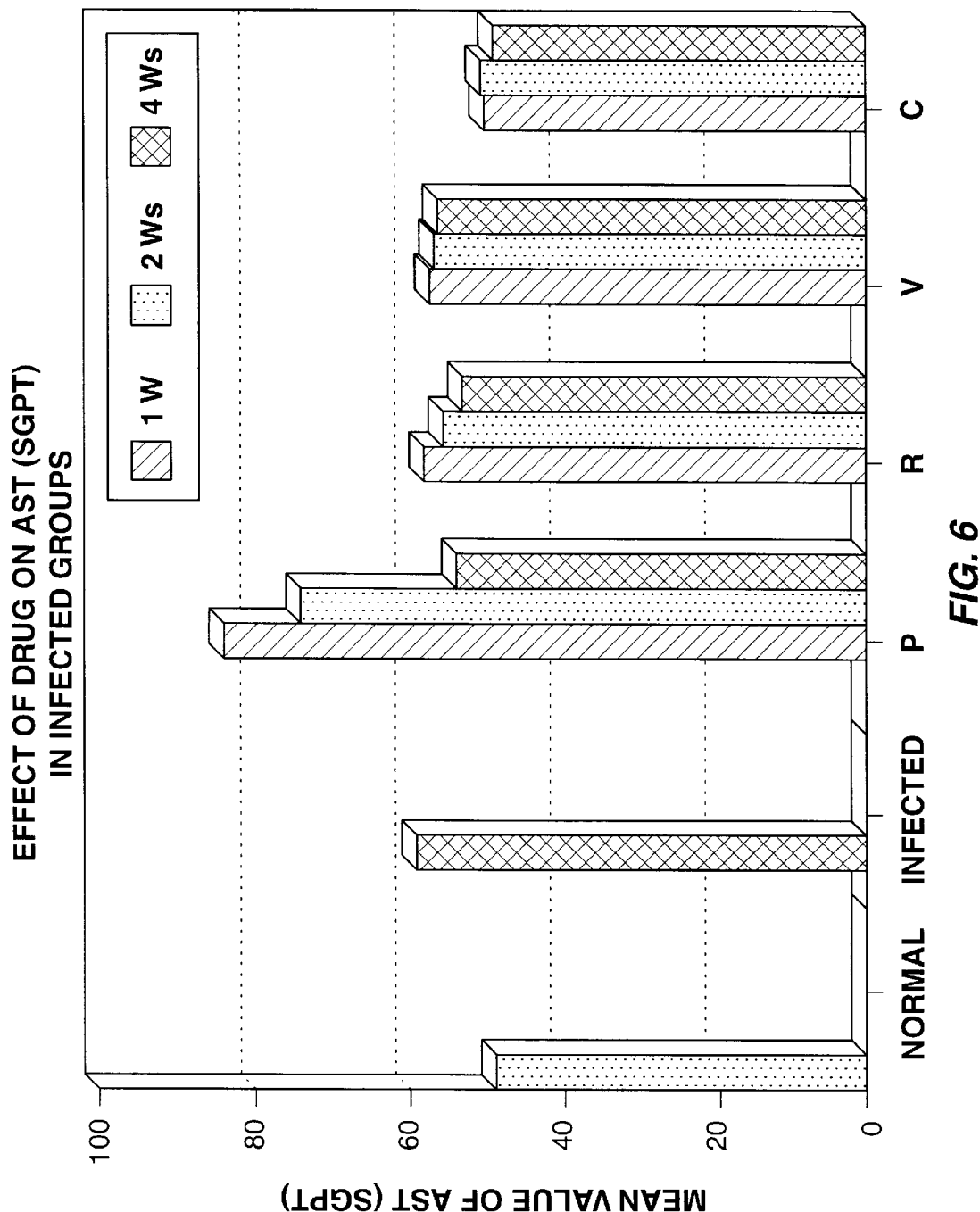
FIG. 6 is a graph of the effect of treatment on ALT (SGPT) in infected groups.
Figure 7:
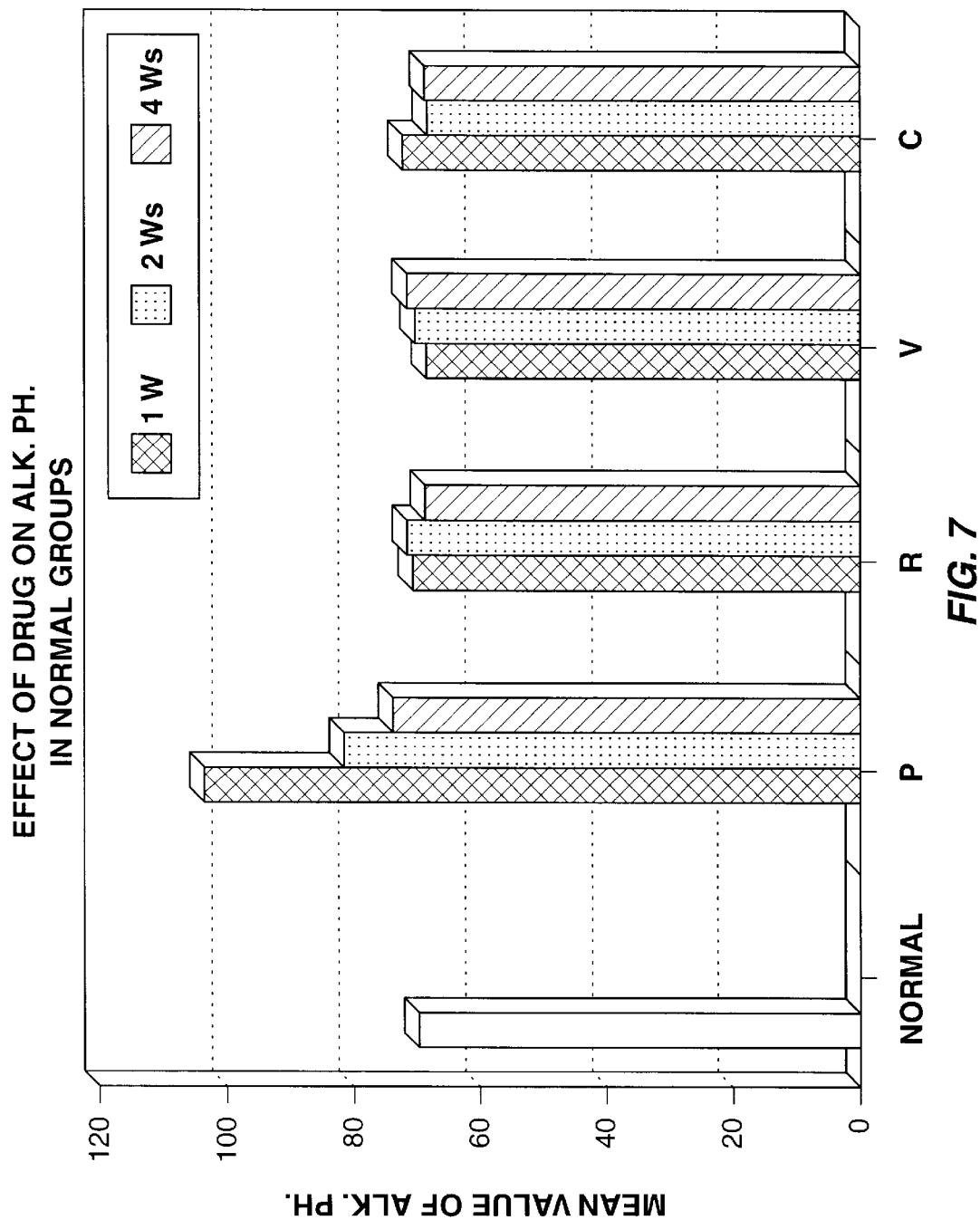
FIG. 7 is a graph of the effect of treatment on alkaline phosphatase in normal groups.
Figure 8:
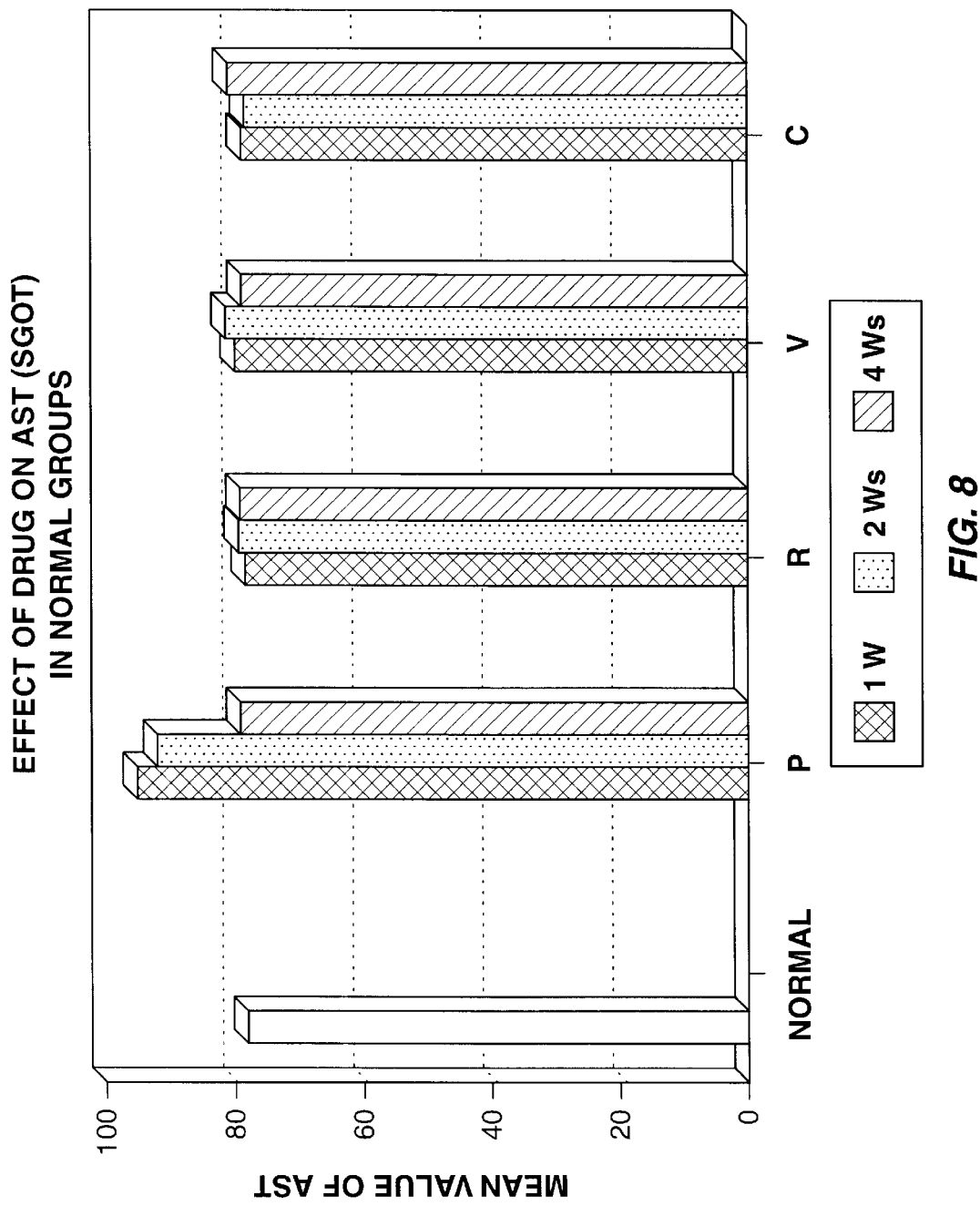
FIG. 8 is a graph of the effect of treatment on AST (SGOT) in normal groups.
Figure 9:
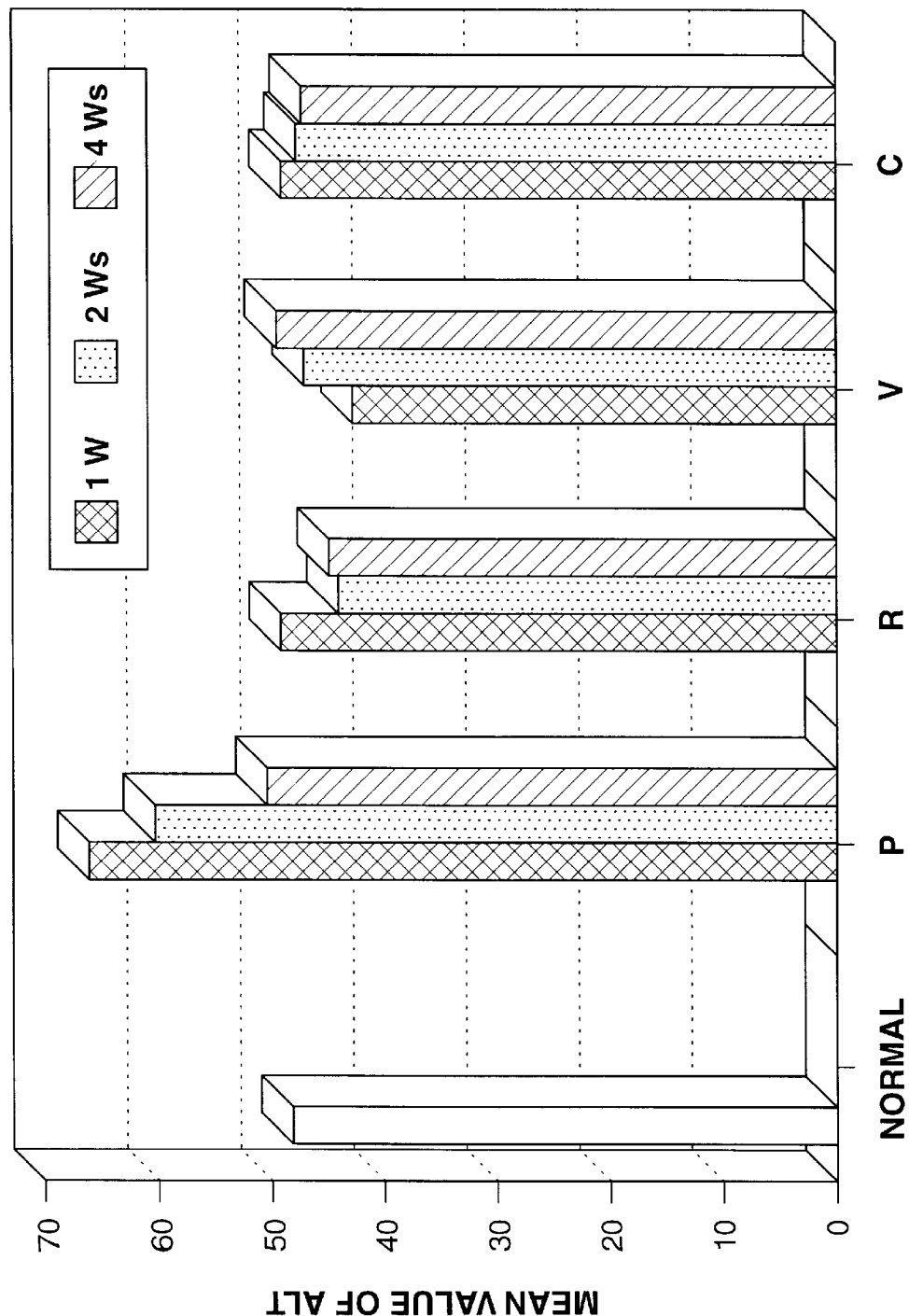
FIG. 9 is a graph of the effect of treatment on ALT (SGPT) in normal groups.

The drug has resulted in a marked reduction in worm load reaching 100% two weeks after treatment in the group that received the combination therapy (Table 1 and FIG. 1). Furthermore, the drug caused effective oogram changes with more antischistosomal activity in the groups that received the combination therapy and the crude plant (Table 2). There was significant reduction in the number of ova in the liver and intestine which was more evident in groups that received the combination therapy and the crude plant and the maximal reduction was reached after one month (Table 3 and FIGS. 2 and 3). The estimated serum enzymes showed transient rise noticed one week post treatment only in groups that received the crude plant (infected treated group and non-infected normal treated group) and levels were normalized one week later (Table 4 and FIGS. 4, 5 and 6). On the other hand, resin, volatile oil and combination therapy did not cause any significant changes in enzyme levels in all normal non-infected groups all through the period of the experiment (Table 5 and FIGS. 7, 8 and 9).

From the above results, the conclusion was reached that combination therapy is the best schistosomicidal drug for the following reasons: 1) combination therapy did not cause initial rise in serum enzyme levels; 2) it took shorter time (2 weeks) to cause 100% reduction in worm load; and 3) it caused more pronounced reduction in number of ova in liver and intestine.

REFERENCES

Al-Awadi, F.; Fatania, H.; Shamte, U. (1991) Diabetes Res. 18(4):163–8.

Al-Harbi, M. M.; Quresh, S.; Raza, M.; Ahmed, M. M.; Giangreco, A. B.; Shah, A. H. (1994): Chemotherapy, 40(5) :337–47.

Claeson, P.; Radstrom, P.; Skold, O.; Nilsson, A.; Hoglund, S. (1992): Phytotherapy Research, 6(2):94–8.

Claeson, P.; Andersson, R.; Samuelesson, G. (1991): Planta. Med., 57(4):352–6.

DeWitt, B. W. (1965): Am. J. Trop. Med. Hyg., 149(4) :579–80.

Food Chem. Technol. (1992): 30(Suppl.):915–25.

Lee, T. Y.; Lam, T. H. (1993): Contact Dermatitis, 28(2) :89–90.

Michie, C. A. and Cooper, E. (1991): J. Roy. Soc. Med., 84:602–4.

Pellegrino, J. and Squeira, A. F. (1956) : Rev. Bras. Molar, 8:589–97.

Pellegrino, J. Oliveira, C. V.; Faria, J. and Cunha, A. S. (1962): Am. J. Trop. Med. Hyg., 11(2):201–25.

Pellegrino, J. and Faria, J. (1965) : Am. J. Trop. Med. Hyg., 14(3):363–9.

Pesko, L. J. (1990): Am. Drug., 202:90.

Qureshi, S.; Al-Harbi, M. M.; Ahmed, M. M.; Raza, M.; Giangrese, A. B.; Shah, A. H. (1993): Cancer Chemother. Pharmacol., 33(2):130–8.

Shekhar, K. C. (1991): Drugs, 42(3):379–405.
Zygmunt, P. and Claeson, P. (1991): Phytotherapy Research, 5(3):142-4.

Table 1 below is a chart of the effect of crude plant, resin and volatile oil and a combination thereof on worm distribution in hamsters infected with *S. mansoni cercariae*.

Table 2 is below a chart of the effect of crude plant, resin and volatile oil and a combination thereof on intestinal oogam of infected hamsters with *S. mansoni cercariae*.

Table 3 below is a chart of the number of ova per gram of liver and intestine in hamsters receiving resin, volatile oil and a combination thereof.

Table 4 below is a chart of the effect of crude plant, resin and volatile oil and a combination thereof on liver functions of infected hamsters.

Table 5 below is a chart of the effect of crude plant, resin and volatile oil and a combination thereof on liver functions of non infected normal hamsters.

TABLE (1)

Effect of crude plant (P), resin (R), volatile oil (V) and combination therapy; resin with volatile oil (C) on worm distribution in hamster infected with *S. mansoni* cercariae.

| | Total No. of worms per hamster | Portal vein & Mesmery | | Liver | | % of worms in liver | % reduction of worms |
|---|---|---|---|---|---|---|---|
| | | Male | Female | Male | Female | | |
| Infected group | 68.4 ± 22.7 | 25.4 ± 8.2 | 27.3 ± 6.9 | 8.5 ± 2.3 | 7.6 ± 2.1 | 23.5 | — |
| Gr. treated with (P) | | | | | | | |
| 1 week PT | 2.1 ± 0.8 | 0.2 ± 0.7 | 0.3 ± 0.1 | 0.7 ± 0.2 | 0.9 ± 0.2 | 76.2 | 96.6 |
| 2 weeks PT | 1.8 ± 0.7 | 0.8 ± 0.2 | 0.7 ± 0.2 | 0.2 ± 0.04 | 0.1 ± 0.05 | 16.7 | 97.4 |
| 4 weeks PT | 0.0 | 0.0 | 0.0 | 0.0 | 0.0 | 0.0 | 100 |
| Gr. treated with (R) | | | | | | | |
| 1 week PT | 17.1 ± 4.5 | 1.3 ± 0.4 | 2.1 ± 0.6 | 6.5 ± 1.6 | 7.2 ± 2.3 | 80.1 | 75 |
| 2 weeks PT | 13.7 ± 3.6 | 5.5 ± 1.6 | 6.2 ± 1.1 | 6.6 ± 0.1 | 1.4 ± 0.4 | 14.6 | 80 |
| 4 weeks PT | 12.3 ± 3.2 | 4.1 ± 1.2 | 6.2 ± 1.5 | 1.0 ± 0.2 | 1.0 ± 0.4 | 16.3 | 82 |
| Gr. treated with (V) | | | | | | | |
| 1 week PT | 8.5 ± 4.3 | 2.0 ± 0.5 | 3.6 ± 1.2 | 6.7 ± 1.6 | 6.2 ± 1.7 | 69.7 | 73 |
| 2 weeks PT | 17.1 ± 4.1 | 5.9 ± 1.4 | 8.1 ± 2.1 | 2.0 ± 0.7 | 1.1 ± 0.7 | 18.1 | 75 |
| 4 weeks PT | 13.7 ± 3.2 | 4.8 ± 1.3 | 7.2 ± 2.0 | 0.8 ± 0.3 | 0.8 ± 0.4 | 11.7 | 80 |
| Gr. treated with (C) | | | | | | | |
| 1 week PT | 1.4 ± 0.6 | 0.1 ± 0.5 | 0.2 ± 1.0 | 0.5 ± 0.1 | 0.6 ± 0.2 | 78 | 98 |
| 2 weeks PT | 0.0 | 0.0 | 0.0 | 0.0 | 0.0 | 0.0 | 100 |
| 4 weeks PT | 0.0 | 0.0 | 0.0 | 0.0 | 0.0 | 0.0 | 100 |

PT = Post treatment

TABLE (2)

Effect of crude plant (P), resin (R), volatile oil (V) and combination therapy; resin with volatile oil (C) on intestinal oogram of infected hamsters with *S. mansoni* cercariae.

|  | % of immature ova | | | | % of mature ova in relation to viable ova | % of dead ova | % of hamsters with oogram changes |
|---|---|---|---|---|---|---|---|
|  | stage I | stage II | stage III | stage IV | | | |
| Infected group | 9.4 | 9.5 | 26.5 | 6.7 | 47.3 | 1.5 | — |
| Gr. treated with (P) | | | | | | | |
| 1 week PT | 0.0 | 0.3 | 0.2 | 0.5 | 90 | 71.2 | 100 |
| 2 weeks PT | 0.0 | 0.0 | 0.0 | 0.0 | 100 | 97.2 | 100 |
| 4 weeks PT | 0.0 | 0.0 | 0.0 | 0.0 | 100 | 98.3 | 100 |
| Gr. treated with (R) | | | | | | | |
| 1 week PT | 0.4 | 0.4 | 0.1 | 0.4 | 83.4 | 60.4 | 100 |
| 2 weeks PT | 0.4 | 0.4 | 0.2 | 0.4 | 85.1 | 70.3 | 100 |
| 4 weeks PT | 0.0 | 0.5 | 0.9 | 0.6 | 86.0 | 75.4 | 100 |
| Gr. treated with (V) | | | | | | | |
| 1 week PT | 0.4 | 0.4 | 0.2 | 0.4 | 81.2 | 65.2 | 100 |
| 2 weeks PT | 0.5 | 0.6 | 0.8 | 0.3 | 83.1 | 71.7 | 100 |
| 4 weeks PT | 0.0 | 0.0 | 0.2 | 0.7 | 84.3 | 73.2 | 100 |
| Gr. treated with (C) | | | | | | | |
| 1 week PT | 0.0 | 0.0 | 9.8 | 3.2 | 93.2 | 85.6 | 100 |
| 2 weeks PT | 0.0 | 0.0 | 0.0 | 0.0 | 100 | 98.1 | 100 |
| 4 weeks PT | 0.0 | 0.0 | 0.0 | 0.0 | 100 | 99.5 | 100 |

PT = Post treatment

TABLE (3)

Number of ova per gram liver and intestine in hamsters receiving crude plant (P) resin (R), volatile oil (V) and combination therapy; resin with volatile oil (C).

|  | Liver | Comparison between results 4 weeks post treatment | Intestine | Comparison between results 4 weeks post treatment |
|---|---|---|---|---|
| Infected untreated control group | 11143.2 ± 3268.4 | P & R (HS) | 6538.3 ± 1 | P & R (HS) |
| Gr. treated with (P) | | P & V (HS) | | P & V (HS) |
| 1 week PT | 2117.7 ± 684.5 (HS) | P & C (NS) | 2083.7 ± 482.3 (HS) | P & C (NS) |
| 2 weeks PT | 1820.3 ± 756.8 (HS) | R & V (NS) | 1303.4 ± 415.2 (HS) | R & V (NS) |
| 4 weeks PT | 1026.3 ± 384.7 (HS) | R & C (HS) | 1211.5 ± 428.1 (HS) | R & C (HS) |
| Gr. treated with (R) | | V & C (HS) | | V & C (HS) |
| 1 week PT | 4012.9 ± 985.1 (HS) | | 2750.3 ± 702.8 (HS) | |
| 2 weeks PT | 3119.3 ± 842.5 (HS) | | 1946.1 ± 491.3 (HS) | |
| 4 weeks PT | 2475.1 ± 651.7 (HS) | | 1862.4 ± 328.1 (HS) | |
| Gr. treated with (V) | | | | |
| 1 week PT | 399.2 ± 898.4 (HS) | | 2554.2 ± 814.4 (HS) | |
| 2 weeks PT | 3011.7 ± 803.5 (HS) | | 1837.1 ± 625.1 (HS) | |
| 4 weeks PT | 2101.3 ± 721.3 (HS) | | 1752.1 ± 432.8 (HS) | |
| Gr. treated with (C) | | | | |
| 1 week PT | 1912.2 ± 528.1 (HS) | | 2144.4 ± 518.4 (HS) | |
| 2 weeks PT | 1121.3 ± 317.5 (HS) | | 1274.7 ± 328.9 (HS) | |
| 4 weeks PT | 934.5 ± 226.8 (HS) | | 1045.8 ± 282.3 (HS) | |

HN = Highly significant (P < 0.01)
NS = Non significant (P > 0.05)
PT = Post treatment.

TABLE (4)

Effect of treatment by crude plant (P), resin (R), volatile oil (V) and combination therapy; resin with volatile oil (C) on liver functions of infected hamsters S. mansoni cercariae.

|  | Alkaline phosphatase | AST (SGOT) | ALT (SGPT) |
| --- | --- | --- | --- |
| Normal untreated uninfected group | 69.4 ± 32.4 | 78.3 ± 21.5 | 48.2 ± 14.2 |
| Infected untreated control group | 145.6 ± 43.2 (HS) | 111.5 ± 26.2 (HS) | 58.3 ± 13.3 (HS) |
| Gr. treated with (P) | | | |
| 1 week PT | 178.2 ± 48.9 (HS) | 143.7 ± 34.8 (HS) | 83.4 ± 16.9 (HS) |
| 2 weeks PT | 100.2 ± 30.2 (S) | 95.2 ± 21.42 (S) | 73.4 ± 14.4 (S) |
| 4 weeks PT | 71.1 ± 28.5 (NS) | 84.4 ± 23.6 (NS) | 53.1 ± 13.2 (NS) |
| Gr. treated with (R) | | | |
| 1 week PT | 120.2 ± 33.8 (HS) | 101.5 ± 22.8 (HS) | 57.2 ± 14.1 (S) |
| 2 weeks PT | 112.4 ± 22.4 (HS) | 91.3 ± 23.5 (S) | 54.8 ± 12.4 (S) |
| 4 weeks PT | 96.4 ± 21.6 (S) | 85.1 ± 20.8 (NS) | 52.3 ± 10.3 (S) |
| Gr. treated with (V) | | | |
| 1 week PT | 131.3 ± 35.7 (HS) | 110.4 ± 22.9 (HS) | 56.3 ± 13.8 (S) |
| 2 weeks PT | 120.4 ± 32.8 (S) | 100.4 ± 25.4 (S) | 55.8 ± 11.3 (S) |
| 4 weeks PT | 99.6 ± 24.1 (NS) | 91.8 ± 19.6 (S) | 55.7 ± 12.4 (S) |
| Gr. treated with (C) | | | |
| 1 week PT | 101.1 ± 25.1 (HS) | 100.6 ± 20.3 (S) | 49.3 ± 13.6 (NS) |
| 2 weeks PT | 91.6 ± 26.4 (S) | 90.7 ± 21.2 (S) | 49.7 ± 12.1 (NS) |
| 4 weeks PT | 71.3 ± 18.9 (NS) | 83.2 ± 18.8 (NS) | 48.4 ± 11.8 (NS) |

Significance of comparison with normal untreated uninfected control group:
HS = Highly significant (P < 0.01)
S = Significant (P < 0.05)
NS = Non significant (P > 0.05)
PT = Post treatment.

TABLE (5)

Effect of treatment by crude plant (P), resin (R), volatile oil (V) and combination therapy; resin with volatile oil (C) on liver functions of non infected normal hamsters.

|  | Alkaline phosphatase | AST (SGOT) | ALT (SGPT) |
| --- | --- | --- | --- |
| Normal untreated uninfected group | 69.6 ± 32.4 | 78.3 ± 21.5 | 48.2 ± 14.2 |
| Gr. treated with (P) | | | |
| 1 week PT | 103.3 ± 16.3 (HS) | 95.3 ± 16.3 (S) | 66.1 ± 12.7 (S) |
| 2 weeks PT | 81.4 ± 28.1 (S) | 91.2 ± 27.3 (S) | 60.3 ± 28.3 (S) |
| 4 weeks PT | 73.6 ± 33.8 (NS) | 79.3 ± 18.6 (NS) | 50.4 ± 12.9 (NS) |
| Gr. treated with (R) | | | |
| 1 week PT | 70.3 ± 26.4 (NS) | 78.4 ± 19.5 (NS) | 49.2 ± 11.8 (NS) |
| 2 weeks PT | 71.4 ± 28.2 (NS) | 79.6 ± 24.7 (NS) | 44.3 ± 10.6 (NS) |
| 4 weeks PT | 68.7 ± 20.5 (NS) | 79.5 ± 17.8 (NS) | 45.1 ± 18.8 (NS) |
| Gr. treated with (V) | | | |
| 1 week PT | 68.3 ± 22.6 (NS) | 80.1 ± 28.1 (NS) | 43.2 ± 13.5 (NS) |
| 2 weeks PT | 70.4 ± 25.4 (NS) | 81.7 ± 16.7 (NS) | 47.2 ± 16.2 (NS) |
| 4 weeks PT | 71.5 ± 23.1 (NS) | 79.2 ± 20.4 (NS) | 49.7 ± 14.3 (NS) |
| Gr. treated with (C) | | | |
| 1 week PT | 72.3 ± 21.8 (NS) | 79.2 ± 24.3 (NS) | 49.3 ± 16.1 (NS) |
| 2 weeks PT | 68.4 ± 19.2 (NS) | 78.8 ± 21.9 (NS) | 48.1 ± 11.4 (NS) |
| 4 weeks PT | 68.6 ± 17.9 (NS) | 81.4 ± 19.8 (NS) | 47.8 ± 13.2 (NS) |

Significance of comparison with normal untreated uninfected control group:
HS = Highly significant (P < 0.01)
S = Significant (P < 0.05)
NS = Non significant (P > 0.05)
PT = Post treatment.

From the foregoing description, it will be apparent that the method for making and the anti-schistosomal drug made thereby of the present invention have a number of advantages, some of which have been described above and others of which are inherent in the invention. Also it will be understood that modifications can be made to the method for making and the anti-schistosomal drug made thereby of the present invention without departing from the teachings of the present invention. Accordingly, the scope of the invention is only to be limited as necessitated by the accompanying claims.

I claim:

1. A pharmaceutical composition for treating *Schistosoma mansoni* in vivo consisting essentially of isolated myrrh oil and myrrh resin as the active ingredients therein, which are extracted from the plant, *Commiphora molmol*, and wherein the ratio of myrrh oil to myrrh resin is approximately 1:2 by weight.

2. The composition of claim 1 further comprising an inert carrier.

3. The composition of claim 1 wherein the composition is encased in a soft gelatin capsule.

4. A method of treating *Schistosoma mansoni* in vivo comprising the steps of orally administering the pharmaceutical composition of claim 1 for a period of one to four weeks to a creature being treated in an amount effective to inhibit or kill *Schistosoma mansoni* in vivo.

5. The method of claim 4 wherein the oil is supplied in an amount equal to approximately 30 mg per kilogram of creature body weight.

6. The method of claim 4 wherein the resin is supplied in an amount equal to approximately 60 mg per kilogram of creature body weight.

* * * * *

UNITED STATES PATENT AND TRADEMARK OFFICE
CERTIFICATE OF CORRECTION

PATENT NO.   : 6,077,513                                                              Page 1 of 1
DATED         : June 20, 2000
INVENTOR(S)  : Ahmed Mohamed Ali Massoud It is certified that error appears in the above-identified patent and that said Letters Patent is hereby corrected as shown below:

<u>Column 2,</u>
Line 4, "(Zygmunt and Claeson, 30 1991)" should be -- (Zygmunt and Claeson, 1991) --
Line 18, delete "dr"

Signed and Sealed this

Seventeenth Day of September, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO.   : 6,077,513
DATED        : June 20, 2000
INVENTOR(S)  : Ahmed Mohamed Ali Massoud It is certified that error appears in the above-identified patent and that said Letters Patent is hereby corrected as shown below:

<u>Title page,</u>
Item [30], after "[22] Filed: May 1, 1997" insert:
-- [30] Foreign Application Priority Data
May 2, 1996 (EG)………..380/1996 --

Signed and Sealed this

Ninth Day of September, 2003

JAMES E. ROGAN
*Director of the United States Patent and Trademark Office*